(12) United States Patent
Moore et al.

(10) Patent No.: US 7,771,654 B1
(45) Date of Patent: Aug. 10, 2010

(54) APPARATUS FOR MONITORING GASEOUS COMPONENTS OF A FLUE GAS

(76) Inventors: Randall P. Moore, 302 Herrell La., Powell, TN (US) 37849; Robert L. Mullowney, Jr., 378 Naiche Ct., Columbus, OH (US) 43085

( * ) Notice: Subject to any disclaimer, the term of this patent is extended or adjusted under 35 U.S.C. 154(b) by 898 days.

(21) Appl. No.: 11/517,497

(22) Filed: Sep. 7, 2006

(51) Int. Cl.
  G01N 27/27 (2006.01)
  G01N 27/416 (2006.01)
  G01N 27/04 (2006.01)
  G01N 27/403 (2006.01)

(52) U.S. Cl. .................. 422/62; 422/82.01; 422/82.02; 422/83; 422/90; 422/93; 422/98; 436/113; 436/116; 436/117; 436/118; 436/122; 436/149; 436/181

(58) Field of Classification Search .................. 422/62, 422/82.01–82.02, 83, 90, 93, 98; 436/113, 436/116–118, 122, 149, 177, 181
See application file for complete search history.

(56) References Cited

U.S. PATENT DOCUMENTS

| | | | | |
|---|---|---|---|---|
| 4,141,800 A | * | 2/1979 | Breuer et al. | 205/779.5 |
| 4,173,886 A | * | 11/1979 | Archbold et al. | 73/31.02 |
| 4,188,190 A | * | 2/1980 | Muraki et al. | 436/55 |
| 4,191,541 A | * | 3/1980 | Jenkins | 73/863.12 |
| 4,197,177 A | | 4/1980 | Proctor | |
| 4,315,753 A | | 2/1982 | Bruckenstein et al. | |
| 4,325,911 A | * | 4/1982 | Vincent | 422/75 |
| 4,432,939 A | * | 2/1984 | Watanabe et al. | 422/93 |
| 4,670,405 A | | 6/1987 | Stetter et al. | |
| 4,786,472 A | * | 11/1988 | McConnell et al. | 422/61 |
| 4,818,348 A | | 4/1989 | Stetter | |
| 5,168,065 A | * | 12/1992 | Jankura et al. | 436/55 |
| 5,246,668 A | * | 9/1993 | MacCallum et al. | 422/93 |
| 5,601,784 A | * | 2/1997 | Glover et al. | 422/70 |
| 5,621,213 A | | 4/1997 | Barshad | |
| 5,624,546 A | | 4/1997 | Milco | |
| 5,866,075 A | * | 2/1999 | Gupta et al. | 422/88 |
| 5,993,743 A | * | 11/1999 | Nordman et al. | 422/94 |
| 6,207,460 B1 | * | 3/2001 | Kishkovich et al. | 436/106 |
| 6,362,741 B1 | * | 3/2002 | Hickox et al. | 340/605 |
| 6,399,391 B1 | | 6/2002 | Tomlin | |
| 6,528,191 B1 | | 3/2003 | Senner | |
| 6,786,076 B2 | | 9/2004 | Raisanen | |
| 6,830,730 B2 | | 12/2004 | Rhodes | |
| 6,855,557 B2 | * | 2/2005 | Kishkovich et al. | 436/106 |
| 7,029,920 B2 | * | 4/2006 | Lanier et al. | 436/116 |
| 7,209,920 B2 | * | 4/2007 | Olstad et al. | 707/9 |
| 7,442,555 B2 | * | 10/2008 | Nair et al. | 436/113 |

OTHER PUBLICATIONS

Jacquot, R. D. et al, Advances in Instrumentation 1972, 72-730, 17 pp.*

(Continued)

*Primary Examiner*—Arlen Soderquist
(74) *Attorney, Agent, or Firm*—John B. Edel; Kean Miller Hawthorne D'Armond McCowan & Jarman, LLP (57) ABSTRACT

An apparatus for monitoring ammonia in gaseous streams, particularly in flue gas streams. The apparatus is transportable but can be permanently installed. The flue gas can be monitored in real time.

23 Claims, 4 Drawing Sheets

OTHER PUBLICATIONS

Treece, L. C. et al, Environmental Science & Technology 1976, 10, 457-461.*
Mayo, N. et al, Analytica Chimica Acta 1995, 310, 139-144.*
Mellqvist, J. et al, Journal of Quantitative Spectroscopy and Radiative Transfer 1996, 187-208.*
Do, J.-S. et al, Sensors and Actuators B 1996, 37, 19-26.*
Kukla, A. L. et al, Sensors and Actuators B 1996, 37, 135-140.*
Rao, G. S. T. et al, Sensors and Actuators B 1999, 55, 166-169.*
Hodgson, A. W. E. et al, Analytical Chemistry 1999, 71, 2831-2837.*
Currie, J. F. et al, Sensors and Actuators B 1999, 59, 235-241.*
Macken, C. et al, Industrial & Engineering Chemistry Research 2000, 39, 3868-3874.*
Skodras, G. et al, Fuel 2002, 81, 547-554.*
Do, J.-S. et al, Sensors and Actuators B 2002, 86.*
Knake, R. et al, Analytica Chimica Acta 2003, 475, 17-25.*
Tomchenka, A. A. et al, Sensors and Actuators B 2003, 93, 126-134.*
Saxena, V. et al, Sensors and Actuators B 2004, 107, 277-282.*

* cited by examiner

APPARATUS FOR MONITORING GASEOUS COMPONENTS OF A FLUE GAS

FIELD OF THE INVENTION

This invention relates to an apparatus for monitoring ammonia in gaseous streams, particularly in flue gas streams. The apparatus is transportable but can be permanently installed. The flue gas can be monitored in real time.

BACKGROUND OF THE INVENTION

Industrial emissions are a significant source of air pollution. In an attempt to limit the growth of such emissions, many industrialized countries have passed legislation. This legislation typically requires industries, whose emissions are potentially harmful to the environment, to take steps to monitor, control, and to treat the amount and types of emissions that are released into the environment. One such potentially harmful emission is ammonia. Thus, it is desirable to be able to measure the concentration of gaseous ammonia in a variety of environments. In particular, it is often desirable to continuously monitor gaseous ammonia in situ in environments such as flue gas streams, chemical plant feed streams and atmospheric backgrounds. In fact, it has been mandated to continuously monitor the ammonia concentration in flue gases resulting from deNOx processes that introduce ammonia to combustion products in order to convert oxides of nitrogen to $N_2$ and $H_2O$. In such processes, the level of ammonia that must be detected is as low as about 5 parts per million.

Monitoring and analyzing exhaust gases is complicated by the requirement that samples of the exhaust gas must often be taken from flue gas stacks before the exhaust gas is expelled into the atmosphere. Also, gas analysis is generally most conveniently conducted in an enclosed climate-controlled structure on the ground. The distance between sample taking and analysis is especially troublesome when flue gases must be monitored near the outlet of flue gas stacks that are hundreds of feet tall. The distance between gas sampling locations and gas analysis locations has resulted in a variety of conventional monitoring systems. In early monitoring systems, gas analysis equipment was housed at a convenient location on the ground and samples were periodically taken from a probe in the flue gas stack and physically carried to the analysis location. However, transporting samples is inconvenient and often dangerous. In addition, it is desirable in many processes to continuously monitor the components of a gas stream in real time. As mentioned, certain government regulations require continuous monitoring of exhaust gas streams.

In order to achieve continuous and convenient gas monitoring, stack sample probes have been connected to gas analysis equipment through long sample lines. In such systems, a pump near the gas analysis equipment creates suction in the long sample line that pulls gas into the sample probe and down the sample line to the pump whose outlet discharges sample gas into the gas analysis equipment. Continuous monitoring systems with such long sample transport lines are plagued by a number of gas monitoring inaccuracies. For example, when a heated gas sample taken from a flue gas stack is carried the length of a long sample transport line, the potential exists for the sample to cool and certain vapor phase constituents in the sample to condense in the sample transport line. This condensed liquid gathers on the walls of the transport line and collects at low points along the transport line. When a liquid condensate forms in the sample transport line, the condensed liquids tend to absorb gaseous contaminants in the line. Consequently, the absorbed gaseous contaminants will go undetected by the analysis equipment. In addition, the condensate may later emit the absorbed gases, or the condensate may react with a subsequent gas sample resulting in additional inaccuracies. Thus, once liquid forms in the sample transport line, accurate gas monitoring becomes difficult, if not impossible.

To overcome the problem of condensation formation in the sample gas transport line, some conventional systems insulate and heat the sample transport line to prevent condensation between the sampling location and the analysis location. However, gas transport line heaters are typically unreliable and have a tendency to malfunction. After such a malfunction is discovered, it is necessary to turn off the monitoring system and clean condensate out of the gas transport line. Such maintenance is both expensive and time consuming.

Another approach to overcoming the problems associated with long sample transport lines has been to move the gas analyzer to a location close to the gas sample probe. In such systems, the gas analyzer is sometimes mounted on the flue gas stack near the sample probe and the analysis results are transmitted to a convenient location where the results are displayed on a terminal and/or printed. Unfortunately, many gas analyzers are too large, or too sensitive, to be mounted on a flue gas stack and regular maintenance and calibration of gas analyzers is made inconvenient and costly by locating analyzers on the flue gas stack.

Another problem associated with long sample transport lines in conventional monitoring systems is that the gas samples are pulled from the sample probe to the analyzer under suction. If there are any leaks in the long sample transport line, the suction will pull ambient air into the sample creating inaccuracy and system contamination.

Therefore, there is need in the art for improved ammonia analyzers that are portable, more efficient and less expensive to operate.

SUMMARY OF THE INVENTION

In accordance with the present invention, there is provided an apparatus for measuring the concentration of ammonia in a gaseous sample, which apparatus comprises:

a) an enclosure having a plurality of enclosing panels, wherein one panel is a top panel and one panel is a bottom panel and the remaining panels are side panels;

b) at least one inlet for receiving a gaseous sample;

c) at least one outlet for exhausting a gaseous stream;

d) at least one door for accessing the interior of the enclosure;

e) an NO sensor for generating an electrical output in response to the concentration of NO in a gaseous sample;

f) a receiving means for receiving said electrical output from said NO sensor and visually displaying the concentration of NO;

g) an $NO_2$ sensor for generating an electrical output in response to the concentration of $NO_2$ in said gaseous sample;

h) a means for receiving said indicating output from said $NO_2$ sensor and visually displaying the concentration of $NO_2$;

i) a scrubber for scrubbing $SO_2$ from said gaseous sample;

j) an $SO_2$ sensor for generating an electrical output in response to the concentration of $SO_2$ in said gaseous sample;

k) a receiving means for receiving said electrical output from said $SO_2$ sensor and visually displaying the concentration of $SO_2$;

l) at least one $NH_3$ sensor for generating an electrical output in response to the concentration of $NH_3$ in said gaseous sample;

m) at least one means for receiving said electrical output from said at least one $NH_3$ sensor and visually displaying the concentration of $NH_3$;

n) a heater for raising the temperature of the enclosure; and o) a cooling means for lowering the temperature of the enclosure.

In another preferred embodiment there is also provided, within the enclosure, a flow meter for metering the flow of gas sample to the indicating means.

In still another preferred embodiment there is also provided a means to by-pass the scrubber for scrubbing $SO_2$.

DETAILED DESCRIPTION OF THE INVENTION

The term "flue gas" as used herein is as it is generally known in the art. It is typically a gas that exits to the atmosphere via a flue, or stack, which is a pipe or channel for conveying exhaust gases from a source such as a fireplace, furnace, boiler or generator. The terms "flue gas" and "stack gas" are used interchangeably herein. A preferred source of flue gas, to be treated in accordance with the present invention, is from power plants, including coal-fired plants. The composition of the flue gas will depend on what is burned, but it will typically be comprised of predominantly carbon dioxide, water vapor, heated air and minor amounts of pollutants, such as particulate matter, carbon monoxide, nitrogen oxides, sulfur oxides, and ammonia. Ammonia is sometimes injected into the flue gas stream of deNOx processes to convert nitrogen oxides to nitrogen and water. That is, it is sometimes necessary to reduce the concentrations of the nitrogen oxide gases (NO, $NO_2$) in the flue gas stream by use of a reactive gas, such as ammonia. The ammonia is typically added to the flue gas stream at or near the base of the stack so as to react with the nitrogen oxide constituents of the stack gas and thereby form by chemical reaction, molecular nitrogen and water vapor, such transformed compounds being environmentally significantly more benign than the nitrogen oxides and the injected ammonia gas. It has been found in the operation of some plants, such as fossil fuel-fired facilities, that it is advantageous to add a slight excess of the ammonia over the stoichiometric amount required to transform the nitrogen oxides into molecular nitrogen and water vapor and to monitor the concentration of this excess ammonia in a sample of the remaining flue gases, rather than to monitor the concentration of the molecular nitrogen and water vapor.

Figure 1:
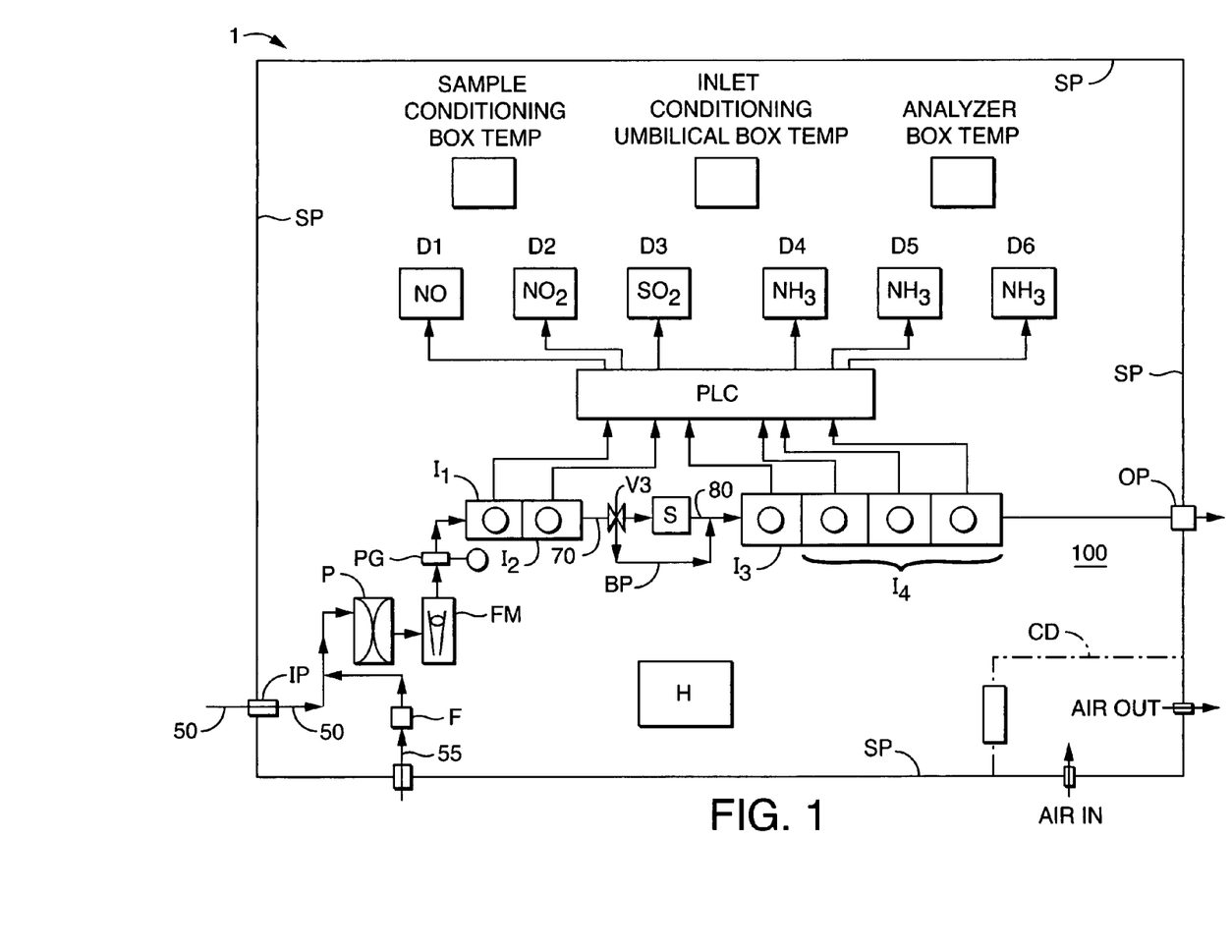
FIG. 1 is a schematic diagram of a preferred embodiment of the ammonia analyzer of the present invention.
Figure 4:
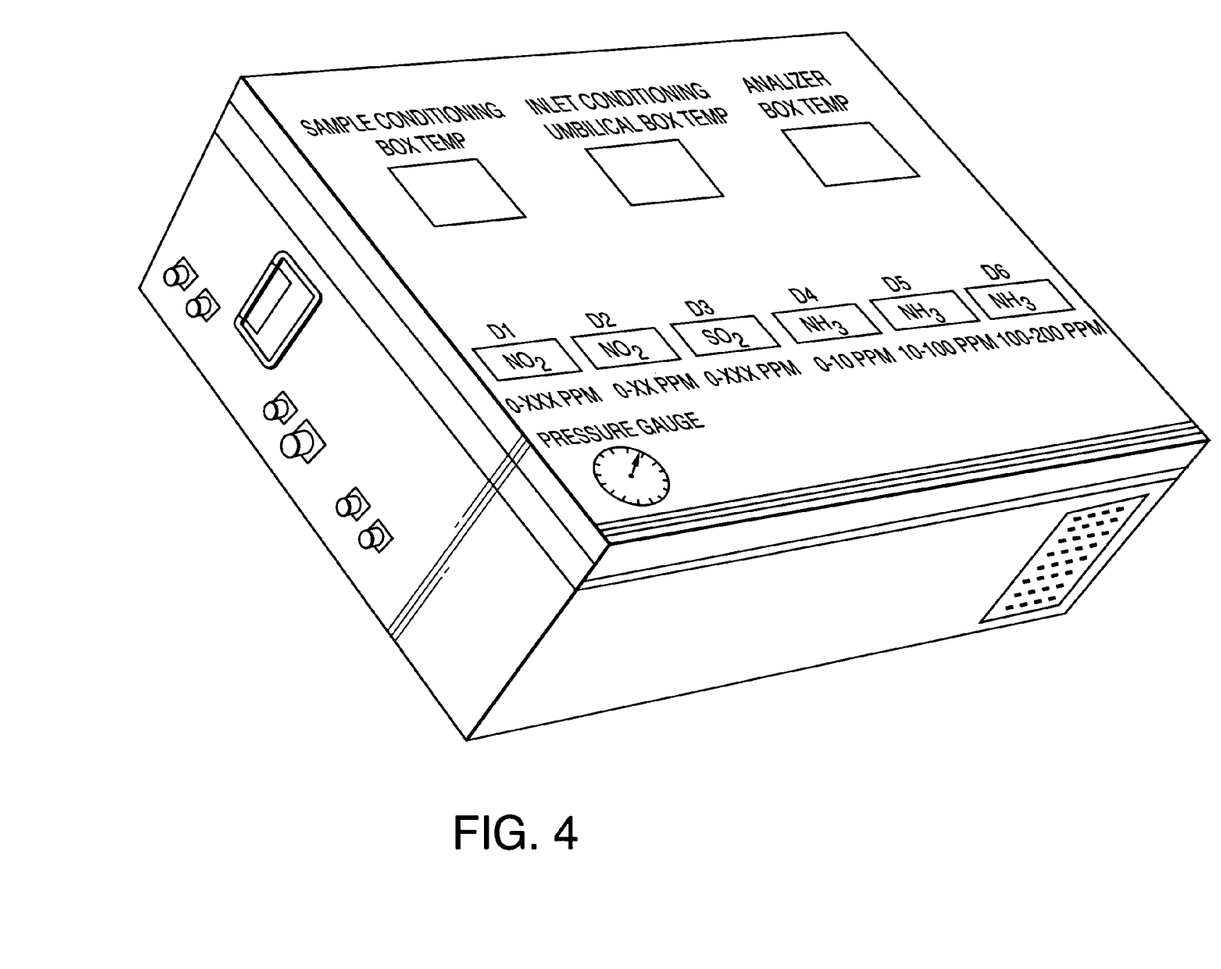
FIG. 4 is a perspective view of an ammonia analyzer box of the present invention showing the cover of FIG. 3 hereof and few preferred features.

The apparatus of the present invention can best be understood with reference to the figures hereof. FIG. 1 hereof is a simplified diagram of a preferred embodiment of an ammonia analyzer 1 of the present invention. The components of the analyzer are contained in an enclosure, or box, having enclosing walls or panels. Although the enclosure can be of any suitable geometric shape, it is preferred that it be rectangular or square in shape, as represented by FIG. 4 hereof. For example, there will preferably be four side panels SP of suitable width, thus defining the depth of the enclosure, a bottom panel BP, and a top panel TP, which will preferably serve as a door for accessing the components contained within the enclosure. A sample of flue gas is obtained directly from a so-called "stack" by use of a suitable flue gas sampling probe. Such probes are well known in the art and may be fabricated from any material compatible with the stack, or flue gas. Typically, these probes are manufactured from high-strength, nickel based, corrosion resistant alloys that may contain other metal components, such as molybdenum and chromium. Such alloys are generally available under the Hastelloy tradename. It is within the scope of this invention that the probe has an inner glass lining.

Figure 2:
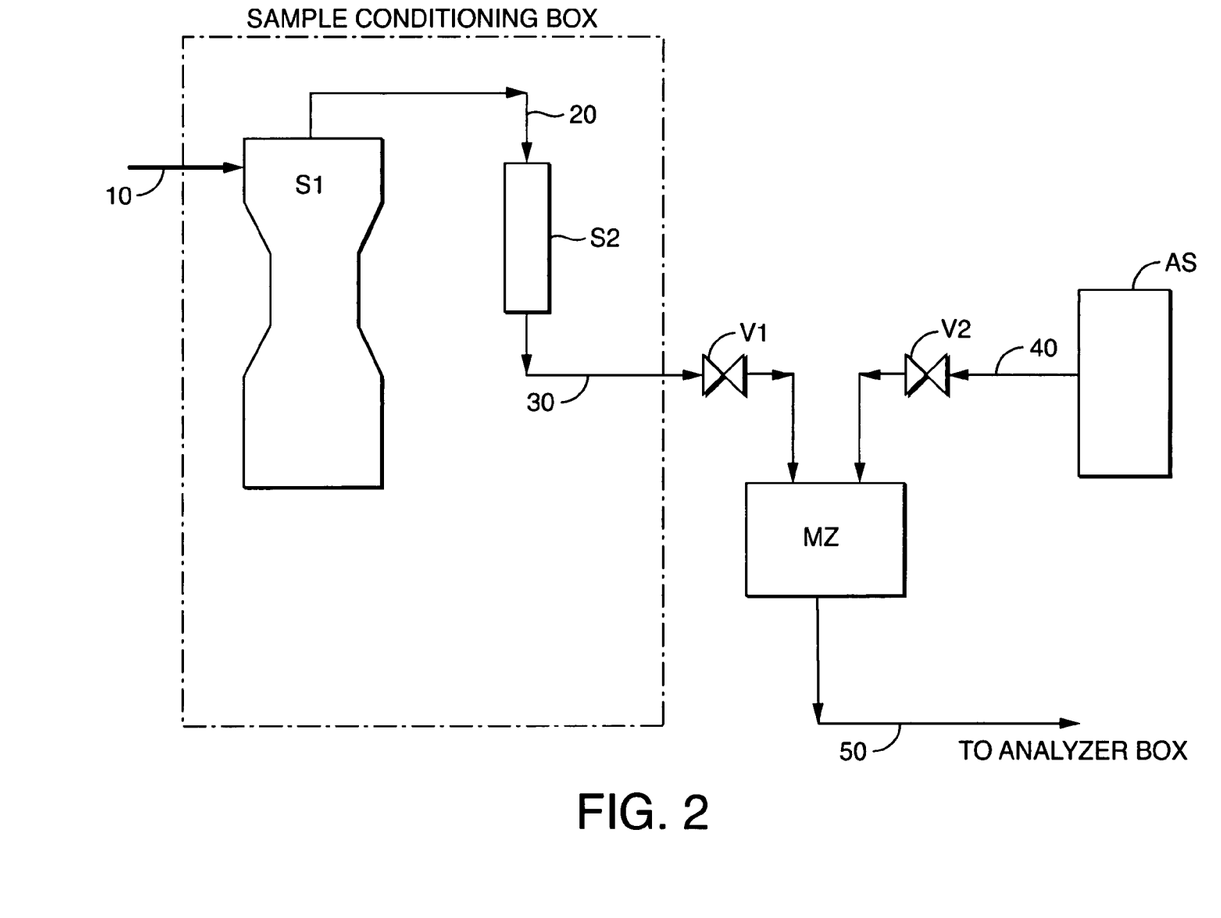
FIG. 2 is a diagram of a preferred embodiment of a preconditioning apparatus for a sample gas introduced into the ammonia analyzer of the present invention.

The sample of flue gas can either be sent directly to the analyzer via line 50 or can first be preconditioned by removing particulates and mixing with a suitable amount of air, preferably substantially moisture and contaminate free air. The ratio of air to flue gas will vary depending on the moisture content of the flue gas and the precise ratio needed can easily be determined by one having ordinary skill in the art. Although the flue gas sample need not be completely dry, it is necessary that the temperature of the flue gas at the electrochemical sensors be above the dew point. Psychrometric charts are readily available and are used to determine the quantity of air that must be added to the flue gas sample to insure that the sample remains in the vapor phase through the sensor area. The dilution rate should be minimized because the detection limit is directly and proportionally impacted thereby. It is preferred that the sample of flue gas be preconditioned such as in a way that is illustrated in FIG. 2 hereof. In FIG. 2 hereof, a sample of flue gas is obtained from the stack via a suitable probe and passed via line 10 to a first separator S1 for removing at least a portion of the particulates that may be present, particularly the larger size particulates. Separator S1 can be any suitable device for separating solids from a gas. Non-limiting examples of such devices include electrostatic precipitation devices and cyclones. Cyclones are preferred. The resulting effluent sample flue gas from separator S1 is optionally, but preferably, passed via line 20 to second separator S2 wherein at least a portion of any remaining particulates, particularly the smaller size particulates are removed, preferably by use of a conventional filtering device such as wire mesh, wedge-wire or sintered stainless steel filter. The resulting substantially solids-free effluent sample flue gas stream from separator S2 is passed via line 30 and valve V1 to mixing zone MZ where it is mixed with a predetermined amount of air, preferably substantially moisture-free air from an air source AS via line 40 and valve V2. The quantity of dilution air varies depending on the temperature and initial moisture content of the sampled gas stream. Sufficient clean dry air is used to maintain the diluted sample above the dew point as the sample passes through the analyzer. A dew point of less than 75° F. or less is typically targeted. It is important throughout this entire sampling process to keep the sample of flue gas above the dew point of any moisture in the sample. Therefore, it is preferred that line 10, the sample conditioning box, mixing zone MZ and line 50 be heated to an effective temperature to maintain the flue gas sample above the dew point. In fact, it is also preferred that the flue gas sample from stack to separator S1 be kept at a temperature close to that of the sample gas as it exits the stack. This temperature will preferably be thermostatically maintained at 300° F.±25° F.

Referring again to FIG. 1 hereof, the sample of flue gas, either preconditioned or not, is passed into analyzer box 1 via line 50 through inlet port IP where it is moved, preferably by use of a suitable pump P, preferably a conventional diaphragm pump of suitable size, and through a gas flow metering device FM of suitable size for the flows required for the electrochemical sensors used herein, typically 1 to 4 liters per minute. It is preferred that the pressure of the sample gas within analyzer 1 be controlled by use of a suitable pressure gas PG before passing the flue gas sample through the electrochemical sensors for analysis. The sample gas is passed to NO sensor $I_1$ that is capable of sensing and measuring the concentration of NO in the sample. NO sensor $I_1$, as well as all of the other sensors used herein to measure the concentration of the various target gases, are preferably electrochemical sensors. It is also preferred that there be a filter (not shown), within the enclosure and upstream of the electrochemical sensors to filter out unwanted gases and any remaining particulates. Electrochemical sensors are essentially fuel cells composed of noble metal electrodes in a suitable electrolyte. The electrolyte is typically an aqueous solution of a strong inorganic acid. When the target gas is detected, the cell generates a small electrical current proportional to the concentration of the target gas in the flue gas sample. Electrochemical sensors suitable for use herein are readily available form such vendors as City Technologies of Great Britain, Delphian Corporation of Northvale, N.J. and Crowcon Detection Instruments, Ltd. Of Erlanger, Ky. As previously mentioned, the electrochemical sensors are chosen for the particular target gas(es) and concentration of target gas(es) to be measured. For example, in the case of NO, the sensor is preferably chosen with a sensitivity of 0 to 100 wppm NO, which will be suitable for most flue gas streams.

The resulting electrical output from NO sensor $I_1$ is transmitted to a programmable logic controller (PLC). PLCs are well known and are widely used in the art. They are typically digital electronic devices that use a programmable memory to store instructions and to implement specific functions such as logic, sequence, timing, counting and arithmetic to control machines and processes. A central processing unit (CPU) is at the heart of a PLC and runs software written for the intended function of the PLC based on its inputs, in this case electrochemical cells, and outputs, in this case means for displaying the concentration of a target gas. The PLC, or equivalent controller, will also control other parameters integral to the measurement of the sample including, but not limited to the heating and cooling devices for the sample conditioning system and umbilical cords and boxes.

The output from the PLC corresponding to the input from sensor $I_1$ is sent to displaying means D1 that is capable of displaying the concentration of NO in the flue gas sample in a predetermined form. It will be understood that the lines in this Figure representing the outputs of each sensor as well as each output of the PLC can be either a hardwire installation as well as a wireless installation and that these lines merely represent the transmission of electrical signals. In fact, there may also be a combination of both hardwire and wireless transmissions where one or more such outputs are performed by hardwire and where one or more are performed by wireless. This will be the same for all electrochemical cells and display means used in the present invention. Also, all display means of this invention will be chosen to display the concentration of the target gas in any suitable predetermined form. For example, the concentration can be displayed in analog form via an analog gauge, or it can be displayed as a digital read-out, or it can be displayed by use of a light that is either on or off when the concentration of the target gas is in a given predetermined range or exceeds a predetermined value. It is preferred that the display means display the concentration by way of a light that will be on or off, more preferably on, when the concentration of NO is in a predetermined range. That is, if the concentration of NO is within the 0 to 100 wppm range, then D1 will be on.

The concentration of each target gas can easily be estimated by those having ordinary skill in the art for each source (flue gas) prior to analysis with the apparatus of the present invention so that the appropriate sensor (electrochemical cells) can be chosen. Electrochemical cells typically have the flexibility to be calibrated for several ranges by setting one or more dip switches or by using an electronic means to modify the cell's performance. It is within the scope of this invention that one or more of the electrochemical cells used in the instant invention be obtained with the predesigned range needed for the particular target gas and concentration of target gas. That is, based on a preliminary estimate, the appropriate cell can be selected and installed for each situation.

The target gas sample, after passing through NO sensor $I_1$, is conducted to $NO_2$ sensor $I_2$ where the concentration of $NO_2$ is detected and measured. It is also preferred that $I_2$ be a suitable electrochemical sensor and that it measure the concentration of $NO_2$ in the range of 0 to 50 wppm, preferably in the range of 0 to 20 wppm. An electrical output proportional to the concentration of $NO_2$ is sent to PLC which in turn sends a suitable output signal to display D2 which will display the concentration of $NO_2$ in the sample. The flue gas sample will be conducted from $NO_2$ sensor $I_2$ via line 70, and by-pass line BP if desired, and line 80 to $SO_2$ sensor $I_3$. An electrical output is produced by $SO_2$ sensor $I_3$ that is proportional to the concentration of $SO_2$ in the sample and sent to the PLC then to display means D3 which is capable of receiving the output signal from PLC and displaying the concentration of $SO_2$. Again, like the other display means of this invention it is preferred that the concentration be displayed in the form of a light to indicate that the concentration is within or outside of a predetermined concentration range. In the event that an unacceptable level of $SO_2$ is detected in the gas sample, then valve V3 can be actuated to a position that will allow the sample gas to be passed through $SO_2$ scrubber S, without passing through by-pass line BP. Valve V3 can also be controlled by the PLC based on the information it receives from $SO_2$ sensor $I_3$. Scrubber S will remove substantially all of any $SO_2$ in the sample gas before the sample gas is conducted to the ammonia detecting electrochemical sensors $I_4$. Since an acid gas, such as $SO_2$ is detrimental to ammonia sensors it is desirable to remove as much of the $SO_2$ from the gas sample as possible. $SO_2$ scrubbing devices are well known in the art and typically contain a basic material to neutralize the $SO_2$. A preferred $SO_2$ scrubbing material is comprised of alkali material preferably sodium hydroxide, and preferably in granular form. The housing for the scrubbing device can be comprised of a suitable material that can withstand a corrosive environment, such as glass silicate coating available from Restek Performance Coatings of Bellefonte, Pa. Although not wishing to be bound by theory we believe that the diluted $SO_2$-containing sample gas passes through the scrubber wherein the $SO_2$ reacts with the sodium hydroxide to form sodium sulfate and water. The water will evaporate and pass through the system and since the pH of ammonia is high it will not react with or adhere to the alkali material.

The gas sample that passes through $SO_2$ sensor $I_3$, which is now substantially free of $SO_2$ is further passed to at least one $NH_3$ sensor $I_4$ that is capable of detecting and measuring the concentration of $NH_3$ in the gas sample. It is preferred that more that one $NH_3$ sensor be used in series and that each $NH_3$ sensor be capable of measuring progressively higher concentration ranges of $NH_3$ than that of the immediate upstream $NH_3$ sensor. It is more preferred that three $NH_3$ sensors be used and that the first $NH_3$ sensor detect $NH_3$ in the range of 0 to 10 wppm, the second in the range of 10 to 100 wppm, and the third in the range of 100 to 200 wppm $NH_3$. Each $NH_3$ sensor will transmit an electrical signal to the PLC relative to the concentration of ammonia that it measures in the range for which it was preprogrammed. The outputs of the PLC corresponding to each $NH_3$ sensor are sent to the respective display means D4, D5, and D6. The flue gas sample, after exiting the last $NH_3$ sensor, will be exhausted to the atmosphere via gas outlet port OP. The sample gas, before exiting the apparatus can optionally be passed through a filter (not shown) to remove any particulates or undesirable component. There will also be provided a heater H for maintaining the enclosure above the dew point of any moisture in the flue gas sample as well as to enhance the accuracy and linearity of the analyzer. Another important function of heater H is to maintain the analyzer box in a preferred temperature range needed for the electrochemical cells to perform with the desired accuracy. This preferred temperature will be about 95° F., plus or minus a few degrees. It is preferred that heater H be an electrical resistance heater. The enclosure will also contain a cooling device CD, preferably an electro-thermal cooling device to help maintain the temperature within the enclosure within the desired tolerance.

Analyzer 1 can also include a display means for the sample conditioning box temperature, the heated sample line temperature, and the analyzer box temperature. It is preferred that all of the display means, including D1-D6 are preferably located on the top panel so that the values of these displays can be viewed without opening the analyzer box. Also, the data obtained and processed by the PLC is preferably sent to a data acquisition and handling system, which will preferably be a CPU in the form of a desktop or laptop computer for reporting, manipulating and storing the data.

After a given analysis run, the electrochemical sensors will need to be refreshed, or regenerated, which can be done by stopping the flow of flue gas sample gas and replacing it with air, preferably filtered air by way of line 55 and filter F. The apparatus of the present invention can also contain a pressure meter (not shown) to measure the pressure of the sample gas flowing through the system. It is preferred that the receiving means for displaying the concentration of the various gases being detected, and the pressure gas, be mounted on the cover, or door, of the apparatus so that the visual display for all target gases can be displayed without opening the analyzer door.

Figure 3:
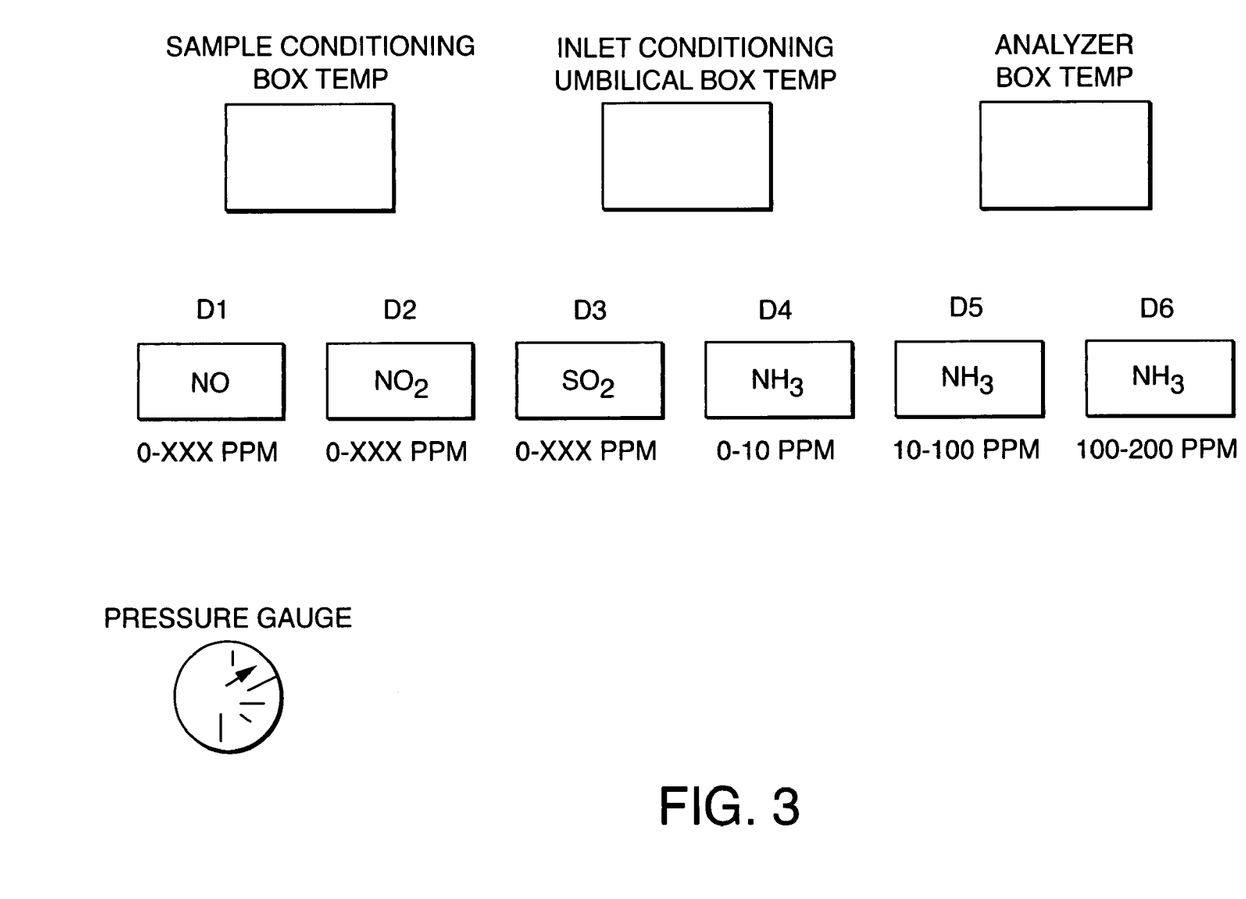
FIG. 3 is a simplified representation of the cover of the ammonia analyzer of the present invention showing some preferred elements.

FIG. 3 hereof illustrates a preferred top panel, which also serves as the door of one embodiment of the enclosure of the present invention. This panel shows a display for the sample conditioning box temperature, the umbilical box temperature and the analyzer box temperatures. It also shows displays D1, D2, D3, D4, D5, and D6 as well as the face of pressure gauge PG. It will be understood that the top panel shown hereof is only a indication of the type of displays that can be a part of this panel and that the top panel can be designed to display any measured element of the analyzer box by any suitable means.

What is claimed is:

1. A flue gas monitoring system for measuring, in real-time, the concentration of gaseous components of a flue gas, which gaseous components include NO, $NO_2$, and ammonia, which flue gas monitoring system comprising:
   a) an enclosure having a plurality of enclosing panels, wherein one panel is a top panel and one panel is a bottom panel and the remaining panels are side panels;
   b) at least one inlet for receiving a gaseous sample;
   c) at least one outlet for exhausting a gaseous stream;
   d) at least one door for accessing the interior of the enclosure;
   e) an NO sensor within the enclosure for generating an electrical output in response to the concentration of NO in a gaseous sample;
   f) a receiving means for receiving said electrical output from said NO sensor and visually displaying the concentration of NO;
   g) an $NO_2$ sensor within the enclosure for generating an electrical output in response to the concentration of $NO_2$ in said gaseous sample;
   h) a means for receiving said indicating output from said $NO_2$ sensor and visually displaying the concentration of $NO_2$;
   i) a scrubber within the enclosure for scrubbing $SO_2$ from said gaseous sample;
   j) an $SO_2$ sensor within the enclosure for generating an electrical output in response to the concentration of $SO_2$ in said gaseous sample;
   k) a receiving means for receiving said electrical output from said $SO_2$ sensor and visually displaying the concentration of $SO_2$;
   l) at least one $NH_3$ sensor within the enclosure for generating an electrical output in response to the concentration of $NH_3$ in said gaseous sample;
   m) at least one means for receiving said electrical output from said at least one $NH_3$ sensor and visually displaying the concentration of $NH_3$;
   n) a heater within the enclosure for raising the temperature within the enclosure; and
   o) a cooling means within the enclosure for lowering the temperature within the enclosure;
   p) wherein there are three sensors for generating an electrical output in response to the concentration of ammonia and wherein said three sensors are in series wherein the first sensor is calibrated for a lower ammonia concentration, the second for a mid range ammonia concentration and the third for a higher ammonia concentration.

2. The flue gas monitoring system of claim 1 which enclosure is rectangular in shape having four side panels, a bottom panel and a top panel which serves as a door.

3. The flue gas monitoring system of claim 1 wherein one or more of the sensors are electrochemical cells.

4. The flue gas monitoring system of claim 3 wherein all of the sensors are electrochemical cells.

5. The flue gas monitoring system of claim 1 wherein at least one of the displaying means for displaying the concentration of the target gas is located on the front panel of the enclosure.

6. The flue gas monitoring system of claim 5 wherein all means for displaying the concentration of all target gases is located on the front panel of said enclosure.

7. The flue gas monitoring system of claim 6 wherein the displaying means are lights that are activated in response to a predetermined concentration of the respective target gas.

8. The flue gas monitoring system of claim 5 wherein the displaying means are lights that are activated in response to a predetermined concentration of the respective target gas.

9. The flue gas monitoring system of claim 5 wherein at least one of the displaying means is an analog gauge.

10. The flue gas monitoring system of claim 5 wherein at least one of the displaying means is a digital read-out device.

11. The flue gas monitoring system of claim 1 wherein there is also provided a solids/gas separation means to separate at least a portion of solids from the flue gas sample prior to it entering the gas inlet port.

12. The flue gas monitoring system of claim 1 wherein there is also provided a means for mixing a predetermined amount of an additive gas to the flue gas sample prior to it entering the gas inlet port.

13. The flue gas monitoring system of claim 1 wherein there is provided a solids separation means for separating at least a portion of the solids from the flue gas sample, followed by a means for mixing an additive gas to the flue gas sample, prior to the flue gas entering the gas inlet port.

14. The flue gas monitoring system of claim 1 wherein there is provided a by-pass means capable of causing the flue gas sample to by-pass the electrochemical cell capable of sensing $SO_2$.

15. A flue gas monitoring system for measuring, in real-time, the concentration of gaseous components of a flue gas, which gaseous components include NO, $NO_2$, and ammonia, which flue gas monitoring system comprising:
   a) a solids/gas separation means for separating solids from a flue gas sample;
   b) a mixing means for mixing a predetermined amount of an additive gas to a flue gas sample;
   c) an enclosure having a plurality of enclosing panels, wherein one panel is a top panel and one panel is a bottom panel and the remaining panels are side panels;
   d) at least one inlet for receiving a gaseous sample;
   e) at least one outlet for exhausting a gaseous stream;
   f) at least one door for accessing the interior of the enclosure;
   g) an electrochemical cell within the enclosure capable of generating an electrical output in response to the concentration of NO in a gaseous sample;
   h) a receiving means for receiving said electrical output from said electrochemical cell capable of sensing NO, and visually displaying the concentration of NO;
   i) an electrochemical cell within the enclosure capable of generating an electrical output in response to the concentration of $NO_2$ in a flue gas sample;
   j) a means for receiving said indicating output from said electrochemical cell capable of sensing $NO_2$, and visually displaying the concentration of $NO_2$;
   k) a scrubber within the enclosure for scrubbing $SO_2$ from said gaseous sample;
   l) an electrochemical cell within the enclosure capable of generating an electrical output in response to the concentration of $SO_2$ in said gaseous sample;
   m) a receiving means for receiving said electrical output from said electrochemical cell capable of sensing $SO_2$, and visually displaying the concentration of $SO_2$;
   n) at least one electrochemical cell within the enclosure capable of generating an electrical output in response to the concentration of $NH_3$ in said gaseous sample;
   o) at least one means for receiving said electrical output from said at least one electrochemical cell capable of sensing $NH_3$, and visually displaying the concentration of $NH_3$;
   p) a heater within the enclosure for raising the temperature within the enclosure;
   q) a cooling means within the enclosure for lowering the temperature within the enclosure; and
   r) a manifold and gas handling line within the enclosure in which the flue gas comes in contact a suitable material such as glass or stainless steel lined with a silicate;
   s) wherein there are three sensors for generating an electrical output in response to the concentration of ammonia and wherein said three sensors are in series wherein the first sensor is calibrated for a lower ammonia concentration, the second for a mid range ammonia concentration and the third for a higher ammonia concentration.

16. The flue gas monitoring system of claim 15 which enclosure is rectangular in shape having four side panels, a bottom panel and a top panel which serves as a door.

17. The flue gas monitoring system of claim 15 wherein at least one of the displaying means for displaying the concentration of the target gas is located on the front panel of the enclosure.

18. The flue gas monitoring system of claim 17 wherein all means for displaying the concentration of all target gases is located on the front panel of said enclosure.

19. The flue gas monitoring system of claim 18 wherein the displaying means are lights that are activated in response to a predetermined concentration of the respective target gas.

20. The flue gas monitoring system of claim 18 wherein at least one of the displaying means is an analog gauge.

21. The flue gas monitoring system of claim 18 wherein at least one of the displaying means is a digital read-out device.

22. The flue gas monitoring system of claim 17 wherein the displaying means are lights that are activated in response to a predetermined concentration of the respective target gas.

23. The flue gas monitoring system of claim 15 wherein there is provided a by-pass means capable of causing the flue gas sample to by-pass the electrochemical cell capable of sensing $SO_2$.

* * * * *